United States Patent [19]

Takaki et al.

[11] Patent Number: 5,179,224
[45] Date of Patent: Jan. 12, 1993

[54] PREPARATION PROCESS OF CINNAMATE ESTER

[75] Inventors: Usaji Takaki, Fujisawa; Yoshihiro Yamamoto, Yokohama; Toshio Matsuhisa, Shimonoseki; Isamu Sudo; Shinobu Aoki, both of Yokohama, all of Japan

[73] Assignee: Mitsui Toatsu Chemicals, Incorporated, Tokyo, Japan

[21] Appl. No.: 769,481

[22] Filed: Oct. 1, 1991

Related U.S. Application Data

[63] Continuation of Ser. No. 29,683, Mar. 24, 1987, abandoned.

[30] Foreign Application Priority Data

Apr. 11, 1986 [JP] Japan .................. 61-82342

[51] Int. Cl.$^5$ .................. C07C 67/38; C07C 69/618
[52] U.S. Cl. .................. 560/105; 560/233; 562/406; 562/497; 562/521
[58] Field of Search .............. 560/105, 233; 562/406, 562/497, 521

[56] References Cited

U.S. PATENT DOCUMENTS 3,346,625 10/1967 Fenton et al. .................. 562/406 X
4,661,620 4/1987 Takaki et al. .................. 560/104

FOREIGN PATENT DOCUMENTS 15242 9/1981 Japan .
70836 7/1982 Japan .
169442 5/1985 Japan .
92242 6/1985 Japan .
231630 6/1985 Japan .
169441 9/1985 Japan .................. 560/104
237046 12/1985 Japan .

OTHER PUBLICATIONS

Fenton et al., Chemtech, (Apr. 1972), pp. 220 to 225.

Primary Examiner—Arthur C. Prescott
Attorney, Agent, or Firm—Fisher, Christen & Sabol

[57] ABSTRACT

Disclosed herein is a process for preparing a corresponding cinnamate ester by reacting a styrene compound, carbon monoxide, an alcohol and oxygen by the use of (1) metallic palladium or a compound thereof, (2) a copper compound, (3) a compound of at least one metal selected from Groups 4A, 5A, 7A, 8A (the iron group only) and 2B in the Periodic Table and (4) a halogen compound as a catalyst which comprises treating the catalyst components recovered from the reaction liquid after completion of the reaction with an oxidizing agent in the presence of an organic acid to regenerate their catalytic activity, using the resulting catalyst components again in the reaction as a catalyst and repeating the foregoing procedure.

The regenerated catalyst is recovered in catalytic activity to the extent of that of a fresh catalyst and thus gives a high reaction performance in the subsequent reaction. Thus, the catalyst containing expensive metal can be used circulatively.

10 Claims, No Drawings

PREPARATION PROCESS OF CINNAMATE ESTER

This application is a continuation of prior U.S. application Ser. No. 07/029,683 filing date Mar. 24, 1987 now abandoned.

BACKGROUND OF THE INVENTION

1) Field of the Invention

This invention relates to a process for preparing cinnamate esters by the reaction of styrene compounds, carbon monoxide, alcohols and oxygen.

2) Description of the Prior Art

Cinnamate esters have found wide-spread commercial utility as perfumes and raw materials therefor owing to their inherent aroma. They are also important as raw materials for chemical or biochemical products, for instance, agricultural chemicals, photosensitive resins and phenylalanine.

Cinnamic acid has conventionally been produced on small scales by using benzaldehyde and derivatives of acetic acid as principal raw materials. This process is however not preferred from the industrial viewpoint since it requires such costly raw materials. As processes permitting use of more economical raw materials, several processes have been proposed to prepare a cinnamate ester by reacting a styrene compound, carbon monoxide, an alcohol and oxygen in the presence of a catalyst (see, for example, Japanese Patent Laid-Open Nos. 15242/1981, 70836/1982, 92242/1985 and 169442/1985).

All of these proposals employ as a catalyst at least metallic palladium or a compound thereof, with various compounds added for the purpose of attaining further increased reaction performances.

On account of the use of such an expensive metal as palladium, it is indispensable not only to develop a catalyst system which can afford a high reaction performance and has a prominent catalytic activity but also to establish a process for the repeated use of the catalyst according to which the catalyst components used in the reaction are recovered efficiently and the catalytic activity lost in the reaction is regenerated for its re-use in the reaction, in order to make these processes useful as an industrial preparation process of cinnamate esters.

Several proposals have been made to recover the catalyst components and regenerate their catalytic activity. In Japanese Patent Laid-Open No. 169441/1985, the catalyst components are recovered by filtration together with active carbon from a reaction liquid obtained as s result of the reaction wherein a particular catalyst system that contains palladium supported on active carbon is used as a main catalyst component. The thus-recovered catalyst components are regenerated in catalytic activity by heating them together with an organic acid. This regeneration method is only applicable to the reaction in which a particular catalyst system is used.

Japanese Patent Laid-Open Nos. 231630/1985 and 237046/1985 disclose processes in accordance with which palladium in a reaction liquid after completion of the reaction is adsorbed onto a carbonaceous carrier added prior or subsequent to the reaction, thus permitting recovery of the palladium by filtration. These recovery processes are however applicable only in the presence of a carbonaceous carrier and thus are not universal.

Further, use of a carbonaceous carrier causes the process to be more complicated and in addition, makes it difficult to remove or separate the water and other unfavorable components adsorbed onto the carbonaceous carrier so that the reaction tends to be affected adversely when the catalyst is used repeatedly. Therefore, these processes involve many problems in their industrialization.

SUMMARY OF THE INVENTION

The present inventors formerly made a discovery that in the preparation of a corresponding cinnamate ester by the reaction of a styrene compound, carbon monoxide, an alcohol and oxygen, use of a catalyst comprising (1) metallic palladium or a compound thereof, (2) a copper compound, (3) a compound of at least one metal selected from Groups 4A, 5A, 7A, 8A (the iron group only), and 2B in the Periodic Table and (4) a halogen compound led to the attainment of a high reaction performance and prominent catalytic activity and have applied it already for a patent. Such problem is disclosed in U.S. Ser. No. 780,838, filed on Sep. 17, 1985, now U.S. Pat. No. 4,661,620.

A first object of the present invention is, with a view to making the preparation process of cinnamate esters by reacting styrenes, carbon monoxide, alcohols and oxygen industrially more advantageous, to provide an efficient process which comprises effecting the reaction by using the aforesaid catalyst system capable of affording a high reaction performance and prominent catalytic activity, treating the catalyst components recovered from the resultant reaction liquid to regenerate their catalytic activity to a high level by a simple and easy means and using the catalyst components circulatively in the reaction.

A second object of the present invention is, with a view to rendering the foregoing process more effective, to provide a process according to which the catalyst components can be recovered in a simple and efficient manner.

The present inventors made intensive investigations with the aim of attaining the above objects and found that when a styrene compound, carbon monooxide, an alcohol and oxygen were reacted by the use of a catalyst comprising (1) metallic palladium or a compound thereof, (2) a copper compound, (3) a compound of at least one metal selected from Groups 4A, 5A, 7A, 8A (the iron group only) and 2B of the Periodic Table and (4) a halogen compound and the catalyst components recovered from the resultant reaction liquid were treated with an oxidizing agent in the presence of an organic acid, the catalytic activity of the catalyst components could be regenerated sufficiently in a simple and easy way and the catalyst components could be used again and repeatedly as a catalyst in the reaction, leading to completion of the present invention.

Further, it was also found that when the reaction liquid was concentrated under specific temperature conditions and the concentrated liquid was filtered by a specific method to recover the solid catalyst components in the recovery of the catalyst components from the reaction liquid, the halogen component as well as the metallic catalyst components were recovered collectively with high efficiency by such simple procedures, and when they were treated with an oxidizing agent in the presence of an organic acid, they could be used again and repeatedly in the reaction as a catalyst with their catalytic activity regenerated to a sufficient degree.

Specifically, the present invention provides a process for preparing a corresponding cinnamate ester by reacting a styrene compound, carbon monoxide, an alcohol and oxygen by the use of (1) metallic palladium or a compound thereof, (2) a copper compound, (3) a compound of at least one metal selected from Groups 4A, 5A, 7A, 8A (the iron group only) and 2B in the Periodic Table and (4) a halogen compound as a catalyst which comprises treating the catalyst components recovered from the reaction liquid after completion of the reaction with an oxidizing agent in the presence of an organic acid to regenerate their catalytic activity, using the resulting catalyst components again in the reaction as a catalyst and repeating the foregoing procedure.

Further, the present invention provides, as a more preferable modification, a process for preparing a cinnamate ester which comprises concentrating the reaction liquid obtained as described above at 250° C. or below, filtering the concentrated liquid at 20° C. or above or after adding a hydrocarbon thereto to recover the solid catalyst components, treating the solid catalyst components with an oxidizing agent in the presence of an organic acid to regenerate their catalytic activity, using the resulting catalyst components again in the reaction, and repeating the foregoing procedure.

DETAILED DESCRIPTION OF PREFERRED EMBODIMENTS

As specific styrene compounds useful in the practice of the process of the present invention, may be mentioned styrene, alkyl derivatives of styrene such as α-methylstyrene, β-methylstyrene, α-ethylstyrene, β-ethylstyrene, o-methylstyrene, m-methylstyrene, p-methylstyrene, m-ethylstyrene, p-ethylstyrene, p-tert-butylstyrene and p-isopropyl-β-methylstyrene, and other styrene derivatives having, on their aromatic rings, substituent groups which do not impair the intended reaction, such as p-chlorostyrene, p-methoxystyrene and 3,4-dimethoxystyrene.

As exemplary alcohols, may be mentioned aliphatic alcohols such as methanol, ethanol, propanol, butanol, pentanol, octanol, cyclopentanol and cyclohexanol. These alcohols may contain substitutents which do not impair the reaction, such as halogen and alkoxy groups. These alcohols may each be used in an amount of 0.5–100 moles or preferably 1–50 moles per mole of the styrene. They may be used not only as a reaction raw material but also as a solvent.

In the reaction according to the process of the present invention, solvents may be used so far as they do not impair the reaction. Illustratives of such solvents include aliphatic or alicyclic hydrocarbons such as n-hexane, n-pentane and cyclohexane, aromatic hydrocarbons such as benzene, toluene, xylene, ethylbenzene, chlorobenzene and dichlorobenzene and their substituted compounds, ethers such as diethyl ether, dipropyl ether, ethyl methyl ether, tetrahydrofuran, dioxane and ethylene glycol dimethyl ether, ketones such as acetone, ethyl methyl ketone and acetophenone, esters such as methyl acetate, ethyl acetate and methyl propionate, carbonates such as propylene carbonate and dimethyl carbonate, amides such as dimethylformamide, and nitriles such as acetonitrile and benzonitrile.

As the metallic palladium or compounds thereof, i.e., the first component of the catalyst useful in the practice of the process of the present invention, may be mentioned, for example, metallic palladium supported on a carrier such as silica gel, alumina, silica-alumina, diatomaceous earth, pumice or Molecular Sieves, metallic palladium such as palladium black, zero-valent palladium complexes such as dibenzylidene acetone complexes of palladium and tetrakis(triphenylphosphine) palladium, divalent palladium compounds, for example, palladium halides such as palladium chloride, palladium salts of inorganic acids such as palladium nitrate, palladium salts of organic acids such as palladium acetate, palladium propionate and palladium benzoate, palladium complexes such as bis(acetylacetonato)palladium, cyclooctadiene dichloropalladium complexes, palladium chloride benzonitrile complexes or palladium chloride ammine complexes. Of these, palladium halides or complexes thereof, palladium salts of inorganic acids and palladium salts of organic acids are more favored.

In general, the metallic palladium or compounds thereof may each be used in an amount of 0.1 gram atom or less, or preferably in the range of $5 \times 10^{-6}$ to $1 \times 10^{-2}$ gram atom in terms of palladium atom per mole of the styrene used as a raw material.

The copper compounds as the second component of the catalyst useful in the practice of the process of the present invention may include copper halides such as copper chlorides and copper bromides, copper salts of inorganic acids such as copper carbonates and copper nitrates, copper salts of organic acids such as copper acetates, copper propionates, copper stearates, copper cinnamates and copper benzoates, and complex compounds of copper such as copper acetylacetonate and copper benzolyacetonate. Among others, copper halides such as copper chlorides and copper bromides or copper salts of organic acids such as copper acetates and copper propionates are more preferred. These copper compounds may be used singly or as a mixture of two or more of them. It is preferable that these compounds dissolve entirely in the mixed reaction liquid, but no problems will arise even if they remain partially undissolved. These copper compounds may each be used in an amount in the range of 0.004 to 0.4 gram atom, or preferably in the range of 0.008 to 0.3 gram atom in terms of copper atom per liter of the reaction liquid.

Illustrative of the metal in the compound of metal(s) selected from Groups 4A, 5A, 7A, 8A (the iron group only) and 2B in the Periodic Table categorized as the third component of the catalyst useful in the practice of the process of the present invention may include titanium, zirconium, hafnium, vanadium, niobium, tantalum, manganese, rhenium, iron, cobalt, nickel, zinc, cadmium and mercury. Further, the compounds of these metals may embrace inorganic compounds such as the oxides, hydroxides, halides, oxyhalides, nitrates and carbonates, the salts of aliphatic or aromatic carboxylic acids such as acetic acid, propionic acid, stearic acid, cinnamic acid, succinic acid, benzoic acid and phthalic acid, or the complex compounds such as acetylacetonato complexes and cyclopentadienyl complexes.

Among these metallic compounds, compounds of manganese, cobalt, nickel and zinc are more favored, with halides, organic acid salts or complex compounds of these metals being particularly preferred. These metallic compounds may be used singly or two or more of these compounds may be used at the same time. It is desirable that these compounds dissolve entirely in the mixed reaction liquid, but no problems will be raised even if they remain partially undissolved. These compounds as the third component of the catalyst may each be used in such an amount that the ratio of the metallic atom contained therein to the copper atom present in the mixed reaction liquid is in the range of from 0.01 to 50, or preferably from 0.05 to 10.

Illustrative of the halogen compounds as the fourth component of the catalyst useful in the practice of the process of the present invention may be molecular halogens such as chlorine, bromine and iodine or solutions thereof, hydrogen halides such as hydrogen chloride, hydrogen bromide and hydrogen iodide and solutions thereof, phosphorus halides such as phosphorus trichloride, phosphorus pentachloride, phosphorus tribromide and phosphorus pentabromide, phosphorus oxyhalides such as phosphoryl chloride and phosphoryl bromide, sulfur oxyhalides such as thionyl chloride and thionyl bromide, halogenated telluriums such as tellurium tetrachloride and tellurium tetrabromide, metal halides or metal oxyhalides with corresponding metallic valencies such as titanium chloride, zirconium bromide, vanadium oxytrichloride, molybdenum chloride, manganese chloride, iron chloride, iron iodide, platinum chloride, copper chloride, copper bromide, zinc chloride, tin chloride, antimony chloride and bismuth chloride. The halogen compounds may further include halogen-containing carbonic acid derivatives such as phosgene and methyl chloroformate, tertiary alkyl halides such as tertiary butylchloride and tertiary butylbromide, and organic halogen compounds susceptible to halogen ion generation, for example, acid halides such as acetyl chloride and benzoyl bromide.

Among these, chlorine, hydrogen chloride, hydrogen bromide, phosphorus pentachloride, phosphoryl chloride, vanadium oxytrichloride, chromiun trichloride, manganese chloride, iron chloride, iron bromide, copper chloride, copper bromide, zinc chloride, tin chloride and bismuth chloride are preferred.

These halogen compounds may be used singly or as a mixture of two or more of them. When palladium halides as the first component of the catalyst, copper halides as the second component of the catalyst and/or halides of the metals of Group 4A, 5A, 7A, 8A (the iron group only) or 2B as the third component of the catalyst are used, these halogen compounds may serve as a whole or part of the halogen compound to be used as the fourth component of the catalyst.

The amount of the halogen compound to be used as the fourth component of the catalyst is in the range of from 0.004 to 0.8 gram atom or preferably from 0.008 to 0.6 gram atom in terms of halogen atom per liter of the mixed reaction liquid.

In the process of the present invention, the catalyst which has been recovered from the reaction liquid and regenerated in activity according to the process of the present invention, i.e., the regenerated catalyst, can be used as a catalyst in the reaction. It is not necessary that the compounds contained in the regenerated catalyst are absolutely identical to those used in the initial first reaction.

The gaseous raw materials to be used in the process of the present invention are carbon monoxide and oxygen. Air may also be used as an oxygen source. It is preferable to allow carbon dioxide to be present in the reaction system in view of increased reaction performance and enhanced catalytic activity. These gases may also be diluted with an inert gas such as nitrogen or argon for their use in the reaction in order to avoid falling the atmosphere of the reaction into the explosion range.

The partial pressure of carbon monoxide in the reaction in the practice of the process of the present invention is 50 atmospheres (absolute pressure, the same shall apply hereunder) or less, or preferably in the range of 0.005 to 40 atmospheres. The partial pressure of oxygen is 50 atmospheres or below, or preferably in the range of 0.002 to 30 atmospheres.

Carbon monoxide and oxygen and carbon dioxide or an inert gas if used may be charged collectively in their respective required amounts to the reactor. Alternatively, the requisite gases may be additionally fed thereto either continuously or intermittently or their mixed gas may be caused to flow therethrough either continuously or intermittently. Of these feeding methods, those of additional-feeding and flow-through are more preferred.

The feed gaseous mixture to be subjected to the reaction may be prepared freshly whenever the reaction is carried out. Alternatively, a residual gas or spent gas once used in the reaction may be repeatedly used after the concentrations of the individual gas components have been adjusted as needed.

The process of the present invention may be practiced in reaction form either as batch-reaction or as continuous flow-reaction.

In the process of the present invention, the total pressure of the reaction is generally 500 atmospheres or below, with 1-300 atmospheres being preferred, although it depends on the partial pressures of carbon monoxide and oxygen and that of carbon dioxide or an inert gas if used. The reaction temperature may range from room temperature to 200° C. with 40° C.-160° C. being preferred. The reaction time varies with the reaction conditions, but may generally range from 0.01 to 24 hours with 0.05-10 hours being preferred.

In the manner as described above, a reaction liquid which contains a cinnamate ester and the catalyst components is obtained. In the process of the present invention, (1) the cinnamate ester is separated as the intended product from the reaction liquid by a proper means and the catalyst components are then recovered from the reaction liquid by an adequate method or on the contrary, (2) the catalyst components are recovered from the reaction liquid by an adequate method and then the cinnamate ester is separated therefrom as the intended product by a proper means, the catalyst components thus-recovered being subjected to an oxidation treatment to regenerate their catalytic activity. On this occasion, it is more preferable to recover the catalyst components by concentrating the reaction liquid and separating the catalyst components therefrom through filtration.

In the reaction liquid, the catalyst components are often deposited partially as solid, but the rates of recovery of the catalyst components are not so high in the solid obtained through its direct filtration and separation. In order to recover each of the metallic catalyst components collectively with high efficiency, it is essential to concentrate the reaction liquid.

The concentration in the process of the present invention is carried out by a conventional means such as evaporation or distillation, and its operation is generally carried out at subatmospheric or atmospheric pressure, though it can be effected at any pressure of subatmospheric, atmospheric or superatmospheric. Upon concentration, the temperature is 250° C. or below. Any temperatures higher than this tend to cause the catalyst components to deteriorate, thereby making it difficult to regenerate the recovered catalyst components in catalytic activity. The preferred temperature is in the range of 20°–200° C.

The degree of concentration may vary depending on the kinds and amounts of the styrene, alcohol, solvent if used and catalyst components used in the reaction and the reaction conditions, but the concentration may generally be so effected as to remove 50–100 wt. % or preferably 80–100 wt. % of the alcohol contained in the reaction liquid.

As the concentration proceeds, a large amount of solid comes out by precipitation. The concentrated liquid is in the state of highly concentrated slurry and the viscosity of the liquid is also high. Therefore, the solid liquid separation is effected by filtration at 20° C. or higher, or preferably at a temperature of 40°–120° C., or by adding a hydrocarbon to the concentrated liquid followed by filtration. The both procedures may safely be combined together.

Among the hydrocarbons to be used are saturated aliphatic or alicyclic hydrocarbons such as n-pentane, n-hexane, cyclohexane, methylcyclohexane, 2-methylpentane, 2,2-dimethylbutane, n-heptane, 2,4-dimethylpentane, n-octane and isooctane, and aromatic hydrocarbons such as benzene and toluene. A mixture of these hydrocarbons may also be used. These hydrocarbons may each be used generally in an amount of 0.1–50 times as much as the weight of the concentrated liquid.

The filtration operation may be conducted at any pressure of subatmospheric, atmospheric or superatmospheric, depending on circumstances.

In the recovered catalyst components thus-filtered and separated, the metallic catalyst components and halogen are recovered collectively in high yields, although their forms of compound have not yet been clarified.

As regards a proper means to separate a cinnamate ester from a reaction liquid, the cinnamate ester is deposited in the reaction liquid as crystal when the reaction liquid is cooled so that it can be separated by filtration, in the case where the amount of an alcohol used in the reaction is small. However, it is generally preferable to separate the cinnamate ester by distillation or by vacuum distillation in particular. As described above, the separation by distillation may be effected either (1) prior to the recovery of catalyst components or on the contrary (2) subsequent to the recovery of catalyst components. In the case of above (2) where the catalyst components are recovered first from the reaction liquid, the cinnamate ester is deposited in the liquid as crystal when the filtrate resulted from the recovery is cooled, so that the ester can be separated by filtration.

In order that the recovered catalyst components obtained as described above can be used again in the reaction, they are treated with an oxidizing agent in the presence of an organic acid (hereinafter simply referred to as the oxidation treatment) so as to regenerate their catalytic activity.

Illustrative of the oxidizing agent useful in the oxidation treatment in the process of the present invention includes oxygens such as oxygen, air and ozone or those diluted with an inert gas such as nitrogen or argon, peroxides such as peracetic acid, perbenzoic acid, perphthalic acid, hydrogen peroxide, tertiary butyl peroxide, acetyl peroxide and benzoyl peroxide, nitric acid, nitrogen oxides such as nitrogen pentoxide, dinitrogen trioxide and dinitrogen oxide, or molecular halogens such as chlorine and bromine. These oxidizing agents may be used singly or two or more of them may be used simultaneously or successively. Of these, oxygen or air is more preferred.

The amount of the oxidizing agent to be used may vary depending on the amounts of the metallic catalyst components to be oxidized and the varied degree of their valencies, but may generally be 0.01 mole or more, or preferably in the range of 0.10–1,000 moles per gram atom of the total metals in the recovered catalyst components.

Exemplary organic acids useful in the oxidation treatment in the process of the present invention may include aliphatic or aromatic carboxylic acids such as acetic acid, propionic acid, stearic acid and benzoic acid. The amount thereof to be used is 0.01 mole or more, or preferably in the range of 0.50 to 1,000 moles per gram atom of the total metals in the recovered catalyst components.

The oxidation treatment in the process of the present invention may also be carried out by the use of a solvent. Such a solvent may embrace water, alcohols such as methanol, ethanol, propanol, butanol, pentanol, octanol, cyclopentanol, cyclohexanol and ethylene glycol, ethers such as dimethyl ether, methyl ethyl ether, phenyl ethyl ether, tetrahydrofuran, dioxane and ethylene glycol dimethyl ether, ketones such as acetone, methyl ethyl ketone and acetophenone, esters such as methyl acetate, ethyl acetate and methyl propionate, saturated aliphatic or alicyclic hydrocarbons such as n-pentane, n-hexane, cyclohexane, methylcyclohexane, 2-methylpentane, 2,2-dimethylbutane, n-heptane, 2,4-dimethylpentane, n-octane and isooctane, and aromatic hydrocarbons such as benzene and toluene. Further, these compounds may contain a proper substituent group or groups so far as the oxidation treatment is not thereby obstructed. These solvents may also be used as a mixture of two or more of them. Of these solvents, water, alcohols and esters and mixtures thereof are preferred. These solvents may each be used in an amount of 0.1–100 times as much as the weight of the recovered solid, although the amount may vary depending on circumstances.

It is not always necessary to conduct the oxidation treatment in a homogeneous solution. The treatment may also be conducted in a suspension mixture.

No particular limitations are imposed on the method of the oxidation treatment. The requisite materials may be fed to the oxidation reactor collectively or some of them may be charged thereto either continuously or intermittently. The temperature of the oxidation treatment is generally in the range of 0°–200° C. or preferably in the range of 20°–150° C. The oxidation treatment may be practiced at any pressure of subatmospheric, atmospheric or superatmospheric. However, when the oxidizing agent is a gas, atmospheric or superatmospheric pressure is preferred, and a pressure of 1–50 atmospheres is more preferred. A gaseous oxidizing agent may also be fed through the treatment system by blowing it therein at atmospheric or superatmospheric pressure. The treatment period of time is 20 hours or less, or preferably in the range of 10 minutes to 10 hours.

The regenerated catalyst obtained in the above manner is used in the subsequent reaction for the preparation of the cinnamate ester. For this purpose, the regenerated catalyst may be separated as solid by filtering it from the post-oxidation treatment mixture either as it is or after having been concentrated, or by evaporating the mixture to dryness so as to use it in the subsequent reaction, though depending on the circumstance which may vary with the kinds and amounts of the organic acid and solvent used in the oxidation treatment. Further, the regenerated catalyst may involve a part of the organic acid or solvent and thus be undried so far as the reaction is not thereby disturbed. Furthermore, the post-oxidation treatment mixture as it is or after having undergone a treatment like concentration may also be used in the subsequent reaction unless the reaction is thereby obstructed. In usual, the regenerated catalyst is used in the state of semi-dryness or dryness obtained by concentrating the post-oxidation treatment mixture.

The regenerated catalyst obtained in accordance with the process of the present invention may be used in the reaction, either as it is or as a mixture with fresh catalyst components and/or a regenerated catalyst obtained separately.

The regenerated catalyst is recovered in catalytic activity to the extent of that of a fresh catalyst system and thus gives a high reaction performance in the subsequent reaction.

Thus, it becomes possible to use the catalyst circulatively by repeating the reaction and the catalyst regeneration.

In accordance with the process of the present invention, a corresponding cinnamate ester can be obtained with high reaction performance and prominent catalytic activity by using (1) metallic palladium or a compound thereof, (2) a copper compound, (3) a compound of at least one metal selected from Group 4A, 5A, 7A, 8A (the iron group only) and 2B in the Periodic Table and (4) a halogen compound as a catalyst in the reaction of a styrene compound, carbon monoxide, an alcohol and oxygen. Moreover, the catalyst components, which have been recovered from the reaction liquid after completion of the reaction, can be regenerated in catalytic activity to the extent of that of a fresh catalyst in a simple and easy manner so that they can be used circulatively in the reaction. Further, in accordance with the process of the present invention, the catalyst components can be recovered collectively from the reaction liquid without being separated into each component and moreover with high rates of recovery of the metallic components and halogen compound.

Thus, there is established an industrially very advantageous process for the preparation of cinnamate esters, in accordance with which a catalyst containing expensive metals can be used circulatively.

The present invention will be described in more detail with reference to the following examples.

EXAMPLE 1

In a glass-made cylindrical vessel were charged 35.9 milligrams (0.160 millimole) of palladium acetate, 8.00 grams (40.1 millimoles) of cupric acetate monohydrate and 12.2 grams (49.9 millimoles) of manganese (II) acetate tetrahydrate, followed by the addition of a small amount of methanol. Thereafter, 83.33 grams (800.00 millimoles) of styrene were charged therein, followed by the addition of a solution prepared by dissolving hydrogen chloride in methanol in advance, the concentration of which was measured immediately before the addition (1.25N), so as to bring the amount of hydrogen chloride to 20 millimoles. Then, methanol was added further to bring the total volume to 400 ml. The weight of methanol was about 245.5 grams.

The glass vessel was inserted in a 1 liter autoclave. The stirring blades of the autoclave were made of Teflon and its temperature measurement tube was also protected with glass. While maintaining the total pressure at 51 atmospheres and causing a mixed gas, which was composed of carbon monoxide, oxygen and nitrogen at a partial pressure ratio of 10:5:85, to flow through the autoclave in such a way that its flow velocity was 3.8 1/min. (standard state) at the outlet of the autoclave, the contents were reacted at 100° C. for 3 hours with stirring. During the reaction, the outlet gas was discharged through a water-cooled reflux condenser. After completion of the reaction, the reaction liquid was cooled and the pressure was released. The reaction liquid discharged from the autoclave weighed 362.8 grams. Its analysis by high-speed liquid chromatography revealed that it contained 42.4 millimoles of styrene and 697.6 millimoles of methyl cinnamate. The conversion of styrene was 95%, while the yield of methyl cinnamate (i.e., its yield based on the charged styrene) was 87%. The number of mole of the cinnamate ester produced per gram atom of palladium (hereinafter referred to as turnover number of palladium (Pd)) was 4,400.

This reaction liquid was transferred to a flask where it was concentrated at a temperature of 60°-80° C. by means of a rotary evaporator while reducing the pressure gradually to 20 mmHg and maintaining the eventual pressure for 30 minutes, thereby obtaining 132.2 grams of a concentrated liquid. During this concentration, 95% of the methanol was recovered.

While maintaining the temperature at 60° C., the concentrated liquid was filtered with a glass filter under reduced pressure over about 20 minutes. The solid was washed with a small amount of toluene and dried at 60° C. under reduced pressure, thereby recovering 14.4 grams of solid catalyst components after drying. The analyses with atomic absorption spectrum and ion chromatography revealed that the solid contained 0.13 milligram atom of palladium, 37.3 milligram atoms of copper, 48.9 milligram atoms of manganese and 19.4 milligram atoms of chlorine. The rates of recovery based on the charged amounts were 81%, 93%, 98% and 97% respectively.

Methyl cinnamate could be separated by vacuum distillation from the filtrate and toluene washings resulted from the filtration operation.

The solid catalyst components recovered as described above was added with 120 ml of acetic acid and subjected to the oxidation treatment by blowing therein air at a rate of 600 ml/min. for 5 hours with sufficient stirring under the conditions of atmospheric pressure and 90° C. The resulting mixture was then concentrated to dryness at 80° C. and 15 mmHg to obtain 19.1 grams of a regenerated catalyst. By the analysis according to ESCA, it was observed that at least a part of the metallic components was oxidized by the oxidation treatment. The re-analysis of the regenerated catalyst indicated that the rates of recovery of palladium, copper, manganese and chlorine were 80%, 93%, 97% and 98% respectively based on the respective charged amounts and thus were practically unchanged against those obtained prior to the oxidation treatment.

The raw materials were reacted in exactly the same manner as in the first reaction except that the regenerated catalyst was used as a catalyst. As a result, methyl cinnamate was obtained in a yield of 84% and a turnover number of Pd of 5,200.

When the filtration operation of the concentrated liquid in this example was conducted at a temperature lower than 20° C., the filtration was retarded extremely and in some cases the liquid itself was solidified, thus failing in smooth operation.

EXAMPLE 2

A distillate upto a top temperature of 99° C. was removed by atmospheric distillation from the reaction liquid obtained in exactly the same manner as in the first reaction of Example 1, thereby obtaining 126.3 grams of a concentrated liquid. To the concentrated liquid were added and stirred 60 grams of n-hexane and the mixture was filtered at about 30° C. in the same manner as in Example 1. The filtration was completed in about 5 minutes. Having been washed with a small amount of n-hexane, the solid was dried at 60° C. under reduced pressure. The resulting solid was subjected to the oxidation treatment in the same manner as described in Example 1 and then evaporated to dryness to obtain 19.6 grams of a regenerated catalyst. The rates of recovery of palladium, copper, manganese and chlorine were 81%, 95%, 94% and 96% respectively. The raw materials were reacted in the same manner as in the first reaction except that the regenerated catalyst was used. As a result, methyl cinnamate was obtained in a yield of 85% and a turnover number of Pd of 5,200.

EXAMPLE 3

A reaction liquid obtained in exactly the same manner as in the first reaction of Example 1 was concentrated in the same manner as in Example 1. The concentrated liquid thus-obtained was added with 60 grams of toluene and stirred, followed by the filtration at 20° C. in the same manner as in Example 1. The filtration was completed in about 10 minutes. The solid was washed further with a small amount of toluene and then dried at 60° C. under reduced pressure. The resulting solid was subjected to the oxidation treatment and dried in the same manner as in Example 1 to obtain 18.7 grams of a regenerated catalyst. The rates of recovery of palladium, copper, manganese and chlorine were 79%, 93%, 98% and 97% respectively. The raw materials were reacted in the same manner as in the first reaction by using the regenerated catalyst. As a result, methyl cinnamate was obtained in a yield of 81% and a turnover number of Pd of 5,100.

EXAMPLE 4

Solid catalyst components were recovered in exactly the same manner as in Example 1. The recovered catalyst components were added with 120 ml of a mixed solvent of acetic acid and methanol (1:1 by weight) and then with 25 ml of a 20 wt. % aqueous hydrogen peroxide solution, followed by the oxidation treatment at 50° C. for 30 minutes under stirring. The resulting mixture was concentrated under reduced pressure eventually to dryness at 80° C. and 15 mmHg to obtain 19.30 grams of a regenerated catalyst. The rates of recovery of palladium, copper, manganese and chlorine were 82%, 95%, 95% and 99% respectively. Using the regenerated catalyst, the raw materials were reacted in exactly the same manner as in the first reaction. The yield of methyl cinnamate was 80% while its turnover number of Pd was 4,900.

EXAMPLE 5

Solid catalyst components were recovered in exactly the same manner as in Example 1. The recovered catalyst components and 120 ml of a 20 wt. % aqueous acetic acid solution were charged in a glass-made cylindrical vessel, which was then inserted in a 500 ml autoclave. While maintaining the total pressure at 10 atmospheres and allowing air to flow through the autoclave in such a way that its flow velocity was 500 ml/min. (standard state) at the outlet of the autoclave, the contents were subjected to the oxidation treatment at 80° C. for 3 hours with stirring. After opening the autoclave, the contents were concentrated under reduced pressure eventually to dryness at 80° C. and 15 mmHg. A regenerated catalyst was obtained in an amount of 20.0 grams. The rates of recovery of palladium, copper, manganese and chlorine were 81%, 94%, 98% and 98% respectively. Using the regenerated catalyst, the raw materials were reacted in the same manner as in the first reaction. Methyl cinnamate was obtained in a yield of 84% and a turnover number of Pd of 5,200.

EXAMPLE 6

A regenerated catalyst was obtained in exactly the same manner as in Example 1. The rates of recovery of palladium, copper, manganese and chlorine were 83%, 92%, 95% and 97% respectively. The deficiencies of the respective components due to insufficient recovery were supplemented with palladium acetate, cupric acetate, manganese(II) acetate and hydrogen chloride to attain the same amounts as those of the respective catalyst components used in the first reaction. Thus, a second reaction was conducted. Methyl cinnamate was produced with a yield of 88% and a turnover number of Pd of 4,400. A second regenerated catalyst was obtained repeatedly from the second reaction liquid in exactly the same manner as in Example 1. The rates of recovery of palladium, copper, manganese and chlorine in the second regenerated catalyst were 82%, 89%, 99% and 100% respectively. The deficiency of each component in the second regenerated catalyst was supplemented in the same manner so that a third reaction was conducted. The yield of methyl cinnamate was 86% while its turn-over number of Pd was 4,300.

COMPARATIVE EXAMPLE 1

Catalyst components were recovered in the same manner as in Example 1. Without undergoing the oxidation treatment, the recovered catalyst was used entirely to conduct the reaction in the same manner as in the first reaction. Methyl cinnamate was obtained with an extremely low yield of 22%.

COMPARATIVE EXAMPLE 2

A reaction liquid was obtained in the same manner as in Example 1. The reaction liquid was subjected to atmospheric distillation to distill out methyl cinnamate. The distillation was carried out by heating the reaction liquid eventurely upto a bottom temperature of 270° C. at which it was then maintained for 1 hour. To the distillation residue were added 100 grams of toluene and stirred, followed by the filtration at 20° C. to obtain recovered catalyst components. Thereafter, a regenerated catalyst was obtained in exactly the same manner as in Example 1. The rates of recovery of palladium, copper, manganese and chlorine were 92%, 97%, 99% and 91% respectively. The rate of recovery of palladium was higher than those obtained in other Examples, whereas that of chlorine was lower. Using the regenerated catalyst, the raw materials were reacted in the same manner as in the first reaction. The yield of methyl cinnamate and its turnover number of Pd were as low as 67% and 3,600 respectively.

COMPARATIVE EXAMPLE 3

The procedure of Example 1 was exactly followed except for the use of nitrogen in place of air in the oxidation treatment of Example 1 and acetic acid treated with sufficient nitrogen bubbling, thereby obtaining a final dried solid. The rates of recovery of palladium, copper, manganese and chlorine were 83%, 95%, 97% and 98% respectively. Using the solid as a catalyst, the raw materials were reacted in the same manner as in the first reaction. Methyl cinnamate was obtained with an extremely low yield of 25%.

EXAMPLE 7

In the same vessel as used in Example 1 were charged 14.2 milligrams (0.08 millimole) of palladium chloride, 5.98 grams (30.0 millimoles) of cupric acetate monohydrate, 1.34 grams (10.0 millimoles) of cupric chloride, 12.2 grams (49.9 millimoles) of manganese(II) acetate tetrahydrate and 83.33 grams (800.0 millimoles) of styrene, followed by the addition of methanol to bring the total volume to 400 ml. The methanol added was about 241.4 grams.

The raw materials were reacted in the same manner as in Example 1 except that the total pressure was maintained at 10 atmospheres during the reaction, a feed mixed gas composed of carbon monoxide, oxygen and carbon dioxide at a partial pressure ratio of 8.3:5.4:86.3 was used, and the flow rate of the outlet gas was controlled at 4.2 1/min. The reaction liquid after completion of the reaction weighed 359.7 grams. The conversion of styrene was 93% and the yield of methyl cinnamate was 84% while the turnover number of Pd was 8,400.

The catalyst components were recovered from the reaction liquid in exactly the same manner as in Example 1. The rates of recovery of palladium, copper, manganese and chlorine at this stage were 81%, 92%, 97% and 98% respectively. The recovered catalyst components were subjected to the oxidation treatment in the same manner as in Example 1 to obtain a liquid mixture. The liquid mixture was concentrated not to dryness but to a wet state. The wet mixture was added with 100 ml of methanol and stirred, followed by the transfer to a reaction vessel for the subsequent reaction. Using the regenerated catalyst liquid, the raw materials were reacted in the same manner as in the first reaction. The yield of methyl cinnamate was 81%.

COMPARATIVE EXAMPLE 4

The reaction was conducted and the catalyst components were recovered exactly in the same manner as in Example 7. Further, the recovered catalyst components were subjected to the oxidation treatment in exactly the same manner as in Example 1 except that 120 ml of water was added in place of acetic acid. The resulting mixture was concentrated to dryness in the same manner as in Example 1 to obtain a solid. The rates of recovery of palladium, copper, manganese and chlorine were 80%, 92%, 96% and 99% respectively. Using the solid, the raw materials were reacted in the same manner as in the first reaction. The yield of methyl cinnamate was as low as 56%.

EXAMPLES 8-13

In a glass-made cylindrical vessel were charged the catalyst components shown in Table 1 in the amounts given also in the same table, followed by the addition of a small amount of methanol. Thereafter, 26.06 grams (250.0 millimoles) of styrene was charged in the vessel followed by further addition of methanol to bring the total volume to 125 ml. The vessel was inserted in a 500 ml autoclave. The stirring blades of the autoclave were made of glass and its temperature measurement tube was also protected with glass.

While maintaining the total pressure at 10 atmospheres and causing a mixed gas, which was composed of carbon monoxide, oxygen and nitrogen or carbon dioxide (in Table 1, a mixed gas of carbon monoxide, oxygen and nitrogen was represented by A while a mixed gas of carbon monoxide, oxygen and carbon dioxide was represented by B) at a partial pressure ratio of 8-10:5-6:84-87, to flow through the autoclave in such a way that its fow velocity was 1.2 1/min. (standard state) at the outlet of the autoclave, the contents were reacted at 100° C. for 3 hours with stirring. During the reaction, the outlet gas was discharged through a water-cooled reflux condenser. After completion of the reaction, the autoclave was cooled, the pressure was released and the reaction liquid was taken out of the autoclave. The reaction performances and the turnover numbers of Pd are shown in the Table 1.

The reaction liquid was treated in the same manner as in Example 1 except for the alteration of the filtration temperature to 50° C. to recover the catalyst components. The recovered catalyst components were added with 50 ml of acetic acid and the mixture was subjected to the oxidation treatment by blowing therein oxygen at a rate of 300 ml/min. at atmospheric pressure and 80° C. over 3 hours. The resulting mixture was concentrated at 80° C. and 15 mmHg to dryness to obtain a regenerated catalyst. The rates of recovery of palladium, copper, the metal of the third component of the catalyst, and halogen at this stage are shown in Table 1. Respective catalyst components were added freshly to the regenerated catalyst to make up the deficiency of each component in the regenerated catalyst, thereby reacting the raw materials in the same manner as in the first reaction. The catalyst components added and their amounts and the reaction performances in the second reaction are shown in Table 1.

TABLE 1

| | Charged catalyst components in the first reaction (millimole) | | | | | Performance in the first reaction | |
|---|---|---|---|---|---|---|---|
| Example | Palladium compound | Copper compound | Third component | Halogen compound | Mixed gas | Yield of methyl cinnamate (%) | Turnover number of Pd |
| 8 | Pd(OAc)$_2$ 0.050 | Cu(OAc)$_2$.H$_2$O 9.37 | Co(OAc)$_2$.4H$_2$O 15.0 | CuCl$_2$ 3.12 | A | 79 | 3900 |
| 9 | Pd(OAc)$_2$ | Cu(OSt)$_2$ | Mn(OAc)$_2$.4H$_2$O | MnCl$_2$ | B | 83 | 5200 |

TABLE 1-continued

| | | | | | | | | |
|---|---|---|---|---|---|---|---|---|
| 10 | PdCl$_2$ 0.040 | Cu(OAc)$_2$.H$_2$O 12.5 | Ni(OAc)$_2$.4H$_2$O 15.0 | POCl$_3$ 2.1 | B | 76 | 4800 | |
| 11 | Pd(OAc)$_2$ 0.040 | Cu(OAc)$_2$.H$_2$O 9.4 | Mn(OAc)$_2$.4H$_2$O 15.2 | CuBr$_2$ 3.1 | B | 84 | 5300 | |
| 12 | Pd(OAc)$_2$ 0.040 | Cu(PhCOO)$_2$.2H$_2$O 12.5 | Mn(acac)$_2$.2H$_2$O 15.2 | POCl$_3$ 2.1 | B | 79 | 4900 | |
| 13 | PdCl$_2$ 0.040 | Cu(OAc)$_2$.H$_2$O 12.5 | Zn(OAc)$_2$.2H$_2$O 15.1 | VOCl$_3$ 2.1 | A | 72 | 4500 | |

| | Recovery rates of components in the regenerated catalyst (%) | | | | Added catalyst components in the second reaction (millimole) | | | | Performance in the second reaction | |
|---|---|---|---|---|---|---|---|---|---|---|
| Example | Palladium | Copper | Third component metal | Halogen | Palladium compound | Copper compound | Third component | Halogen compound | Yield of methyl cinnamate (%) | Turnover number of Pd |
| 8 | 83 | 91 | 95 | 100 | Pd(OAc)$_2$ 0.009 | Cu(OAc)$_2$.H$_2$O 1.12 | Co(OAc)$_2$.4H$_2$O 0.75 | 0 | 77 | 3800 |
| 9 | 85 | 90 | 100 | 98 | Pd(OAc)$_2$ 0.008 | Cu(OSt)$_2$ 1.25 | 0 | MnCl$_2$ 0.06 | 81 | 4800 |
| 10 | 82 | 92 | 97 | 96 | Pd(OAc)$_2$ 0.007 | Cu(OAc)$_2$.H$_2$O 1.00 | Ni(OAc)$_2$.4H$_2$O 0.45 | POCl$_3$ 0.08 | 75 | 4700 |
| 11 | 77 | 88 | 99 | 96 | Pd(OAc)$_2$ 0.009 | Cu(OAc)$_2$.H$_2$O 1.38 | Mn(OAc)$_2$.4H$_2$O 0.15 | CuBr$_2$ 0.12 | 87 | 5500 |
| 12 | 84 | 88 | 98 | 97 | Pd(OAc)$_2$ 0.008 | Cu(PhCOO)$_2$.2H$_2$O 1.50 | Mn(acac)$_2$.2H$_2$O 0.30 | POCl$_3$ 0.06 | 80 | 4800 |
| 13 | 78 | 90 | 99 | 97 | Pd(OAc)$_2$ 0.009 | Cu(OAc)$_2$.H$_2$O 1.25 | Zn(OAc)$_2$.2H$_2$O 0.15 | VOCl$_3$ 0.06 | 70 | 4400 |

OAc, OSt, PhCOO and acac represent an acetate group, stearate group, benzoate group and acetylacetonato respectively.

EXAMPLE 14

In a glass-made cylindrical vessel were charged 11.23 grams (0.050 millimole) of palladium acetate, 1.88 grams (9.42 millimoles) of cupric acetate monohydrate, 3.82 grams (15.6 millimoles) of manganese-(II) acetate tetrahydrate and 0.420 gram (3.12 millimoles) of cupric chloride, followed by the addition of a small amount of methanol. To the resulting mixture were added 26.04 grams (250.0 millimoles) of styrene, followed by further addition o methanol to bring the total volume to 125 ml. The glass vessel was then inserted in a 500 ml autoclave. The stirring blades of the autoclave were made of glass and its temperature measurement tube was also protected with glass.

While maintaining the total pressure at 51 atmospheres and causing a mixed gas, which was composed of carbon monoxide, oxygen and nitrogen at a partial pressure ratio of 10:5:85, to flow through the autoclave in such a way that its flow velocity was 1.2 liters per minute (standard state) at the outlet of the autoclave, the contents were reacted at 100° C. for 3 hours with stirring. During the reaction, the outlet gas was discharged through a water-cooled reflux condenser. After completion of the reaction, the autoclave was cooled, its pressure was released and the reaction liquid was taken out of the autoclave. Methyl cinnamate was obtained in a yield of 83.6%.

The reaction liquid was treated in the same manner as in Example 1 except for the alteration of the filtration temperature to 50° C., thereby recovering the catalyst components.

To the recovered catalyst components were added 50 ml of acetic acid, and oxygen were blown into the mixture at a rate of 300 ml/min. at 80° C. over 3 hours under stirring. The resulting mixture was concentrated to dryness at 80° C. and 15 mmHg to obtain a regenerated catalyst. The rates of recovery of palladium, copper, manganese and chlorine are shown in Table 2. In order that the amount of each component was adjusted to that used in the first reaction by supplementing its shortage, the regenerated catalyst was added with palladium acetate, cupric acetate monohydrate, manganese(II) acetate tetrahydrate and cupric chloride in the respective amounts given in Table 2. Using the regenerated catalyst thus-adjusted, a second reaction was carried out in exactly the same manner as in the first reaction.

After completion of the second reaction, the catalyst components were recovered and subjected to the oxidation treatment in the same manner as described above to obtain a regenerated catalyst. Using the regenerated catalyst which has been adjusted in the amount of each catalyst component in the same manner as described above, a third reaction was conducted. This procedure was repeated 10 times in total. The results are shown in Table 2.

TABLE 2

| Number of repetitions or reaction | Yield of methyl cinnamate (%) | Recovery rates of components in the regenerated catalyst | | | | Amounts of added catalyst components (millimole) | | | |
|---|---|---|---|---|---|---|---|---|---|
| | | Pd | Cu | Cl | Mn | Pd(OAc)$_2$ | Cu(OAc)$_2$.H$_2$O | CuCl$_2$ | Mn(Oac)$_2$.4H$_2$O |
| 1st | 83.6 | 80 | 93 | 98 | 99 | 0.010 | 0.82 | 0.06 | 0.16 |
| 2nd | 81.2 | 82 | 95 | 97 | 98 | 0.009 | 0.54 | 0.09 | 0.31 |
| 3rd | 79.7 | 76 | 89 | 100 | 98 | 0.012 | 1.38 | 0 | 0.31 |
| 4th | 82.9 | 79 | 91 | 99 | 100 | 0.011 | 1.10 | 0.03 | 0 |
| 5th | 80.6 | 80 | 89 | 97 | 99 | 0.010 | 1.29 | 0.09 | 0.16 |
| 6th | 85.1 | 75 | 94 | 99 | 98 | 0.013 | 0.72 | 0.03 | 0.31 |
| 7th | 84.9 | 82 | 95 | 98 | 99 | 0.009 | 0.57 | 0.06 | 0.16 |
| 8th | 78.2 | 82 | 90 | 100 | 99 | 0.009 | 0.13 | 0 | 0.16 |

TABLE 2-continued

| Number of repetitions or reaction | Yield of methyl cinnamate (%) | Recovery rates of components in the regenerated catalyst | | | | Amounts of added catalyst components (millimole) | | | |
|---|---|---|---|---|---|---|---|---|---|
| | | Pd | Cu | Cl | Mn | $Pd(OAc)_2$ | $Cu(OAc)_2.H_2O$ | $CuCl_2$ | $Mn(Oac)_2.4H_2O$ |
| 9th | 84.4 | 76 | 88 | 99 | 100 | 0.012 | 1.47 | 0.03 | 0 |
| 10th | 82.6 | 81 | 93 | 97 | 98 | 0.010 | 0.79 | 0.09 | 0.31 |
| 11th | 8.61 | | | | | | | | |

OAc represents an acetate group.

As can be seen from the table, the yields of methyl cinnamate were practically unchanged even with the repeated use of the regenerated catalyst and thus no degradations of the catalyst were observed.

EXAMPLE 15

After the removal of a first distillate from a reaction liquid obtained in exactly in the same manner as in the first reaction of Example 1, the reaction liquid was distilled under the final conditions of a pressure of 5 mmHg, bottom temperature of 120°–130° C. and top temperature of 105°–115° C. Methyl cinnamate was separated in a distillation yield of 98.5%. The distillation residue weighed 16.4 grams. Substantially no methanol was contained in the residue.

The distillation residue was added with 100 grams of toluene, heated to 60° C. and filtered under reduced pressure to recover 13.7 grams of solid catalyst components by weight after drying.

The recovered catalyst components were subjected to the oxidation treatment in the same manner as in Example 1 and dried to obtain 18.5 grams of a regenerated catalyst. The rates of recovery of palladium, copper, manganese and chlorine were 82%, 93%, 99% and 96% respectively. Using the regenerated catalyst, the reaction was conducted in the same manner as in the first reaction. The yield of methyl cinnamate was 80%, while its turnover number of Pd was 4,900.

What is claimed is:

1. A process for preparing a corresponding cinnamate ester, which comprises:
   (a) reacting a styrene compound, carbon monoxide, an alcohol and oxygen by use of the catalyst consisting of components (1) a palladium entity, (2) a copper compound, (3) a compound of at least one metal selected from Groups 4A, 5A, 7A, 8A (the iron group only) and 2B in the Periodic Table and (4) at least one halogen compound selected from the group consisting of chlorine, hydrogen chloride, hydrogen bromide, phosphorus pentachloride, phosphoryl chloride, vanadium oxytrichloride, chromium trichloride, manganese chloride, iron chloride, iron bromide, copper chloride, copper bromide, zinc chloride, tin chloride and bismuth chloride;
   (b) recovering the catalyst components as a solid after completion of the reaction by concentrating the reaction liquid at 250° C. or lower and by filtering the concentrated reaction liquid either at 20° C. or higher or after adding a hydrocarbon thereto;
   (c) treating the recovered catalyst components with an oxidizing agent in the presence of an organic acid to regenerate their catalytic activity;
   (d) using the resulting catalyst components again in the reaction as a catalyst; and
   (e) repeating the foregoing procedure.

2. The process as claimed in claim 1 wherein the second component (2) of the catalyst is a copper salt of an organic acid, and the third component (3) of the catalyst is a compound of a metal selected from the group consisting of manganese, cobalt, nickel and zinc.

3. The process as claimed in claim 1 wherein carbon dioxide is allowed to exist in the reaction system.

4. The process as claimed in claim 1 wherein the styrene compound is selected from the group consisting of styrene, α-methylstyrene, α-ethylstyrene, β-methylstyrene, β-ethylstyrene, o-methylstyrene, m-methylstyrene, p-methylstyrene, m-ethylstyrene, p-ethylstyrene, p-tert-butylstyrene, p-chlorostyrene, p-isopropyl-β-methylstyrene, p-methoxystyrene and 3,4-dimethoxystyrene, wherein the alcohol is selected from the group consisting of methanol, ethanol, propanol, butanol, pentanol, octanol, cyclopentanol and cyclohexanol, wherein the palladium entity is selected from the group consisting of metallic palladium supported on a carrier which is silica gel, alumina, silica-alumina, diatomaceous earth, pumice and a molecular sieve, palladium black, dibenzylidene acetone complexes of palladium, tetrakis(triphenylphosphine) palladium, palladium chloride, palladium nitrate, palladium acetate, palladium propionate, palladium benzoate, bis(acetylacetonato) palladium, cyclooctadiene dichloro palladium complexes, palladium chloride benzonitrile complexes and palladium chloride amine complexes, wherein the copper compound (2) is selected from the group consisting of copper chlorides, copper bromides, copper carbonates, copper nitrates, copper acetates, copper propionates, copper stearates, copper cinnamates, copper benzoates, copper acetylacetonate and copper benzoylacetonate, and wherein the metal compound (3) is a compound of a metal selected from the group consisting of manganese, cobalt, nickel and zinc.

5. The process as claimed in claim 1 wherein the reaction of a styrene compound, carbon monoxide, an alcohol and oxygen is conducted in the presence of a solvent which is selected from the group consisting of n-hexane, n-pentane, cyclohexane, benzene, toluene, xylene, ethylbenzene, chlorobenzene, dichlorobenzene, diethyl ether, dipropyl ether, ethyl methyl ether, tetrahydrofurane, dioxane, ethylene glycol dimethyl ether, acetone, ethyl methyl ketone, acetophenone, methyl acetate, ethyl acetate, methyl propionate, propylene carbonate, dimethyl carbonate, dimethylformamide, acetonitrile and benzonitrile.

6. The process as claimed in claim 1 wherein the concentration in step (b) is conducted at a temperature of 20° C. to 200° C. and the filtration in step (b) is conducted at a temperature of 40° C. to 120° C.

7. The process as claimed in claim 1 wherein the hydrocarbon used in step (b) is selected from the group consisting of n-pentane, n-hexane, cyclohexane, methylcyclohexane, 2-methylpentane, 2,2-dimethylbutane, n-heptane, 2,4-dimethylpentane, n-octane, isooctane, benzene and toluene.

8. The process as claimed in claim 1 wherein the oxidizing agent in step (c) is selected from the group consisting of oxygen, air and ozone or those members diluted with nitrogen or argon, peracetic acid, perbenzoic acid, perphthalic acid, hydrogen peroxide, tertiary butyl peroxide, acetyl peroxide, benzoyl peroxide, nitric acid, nitrogen pentoxide, dinitrogen trioxide, dinitrogen oxide, chlorine and bromine.

9. The process as claimed in claim 1 wherein the treatment step (c) is conducted in the presence of a solvent selected from the group consisting of water, methanol, ethanol, propanol, butanol, pentanol, octanol, cyclopentanol, cyclohexanol, ethylene glycol, dimethyl ether, methyl ethyl ether, phenyl ethyl ether, tetrahydrofuran, dioxane, ethylene glycol dimethyl ether, acetone, methyl ethyl ketone, acetophenone, methyl acetate, ethyl acetate, methyl propionate, n-pentane, n-hexane, cyclohexane, methylcyclohexane, 2-methylpentane, 2,2-dimethylbutane, n-heptane, 2,4-dimethylpentane, n-octane, isooctane, benzene and toluene.

10. The process as claimed in claim 1 wherein the organic acid in step (c) is selected from the group consisting of acetic acid, propionic acid, stearic acid and benzoic acid.

* * * * *